United States Patent [19]

Gray

[11] Patent Number: 4,838,336
[45] Date of Patent: Jun. 13, 1989

[54] HOT METAL SAMPLING

[75] Inventor: Adrian L. Gray, Craighall Park, South Africa

[73] Assignee: Foseco International Limited, Birmingham, England

[21] Appl. No.: 158,621

[22] Filed: Feb. 22, 1988

[30] Foreign Application Priority Data

Feb. 24, 1987 [ZA] South Africa ............ 87/1321

[51] Int. Cl.[4] ........................................ G01N 1/12
[52] U.S. Cl. ................................ 164/4.1; 164/150; 73/864.56; 73/864.59
[58] Field of Search .................. 164/4.1, 150; 73/864.55, 864.56, 864.57, 864.59

[56] References Cited

U.S. PATENT DOCUMENTS

| | | | |
|---|---|---|---|
| 3,221,559 | 12/1965 | Miller, Jr. et al. | 73/864.55 |
| 4,046,016 | 9/1977 | Hackett | 73/864.57 |
| 4,125,024 | 11/1978 | Vierbicky | 73/864.55 |
| 4,699,014 | 10/1987 | Boron | 73/864.55 |

Primary Examiner—Richard K. Seidel
Attorney, Agent, or Firm—Nixon & Vanderhye

[57] ABSTRACT

This invention concerns samplers used for sampling molten metals and comprises a metal mold which is encased in a non-reactive refractory material and located in a slot in the end of an immersion tube engaged within the encasing material, the tube having at least an outer layer of non-reactive refractory material. Further the non-reactive material will provide a glass or glass-like outer surface layer thereto during use.

13 Claims, 1 Drawing Sheet

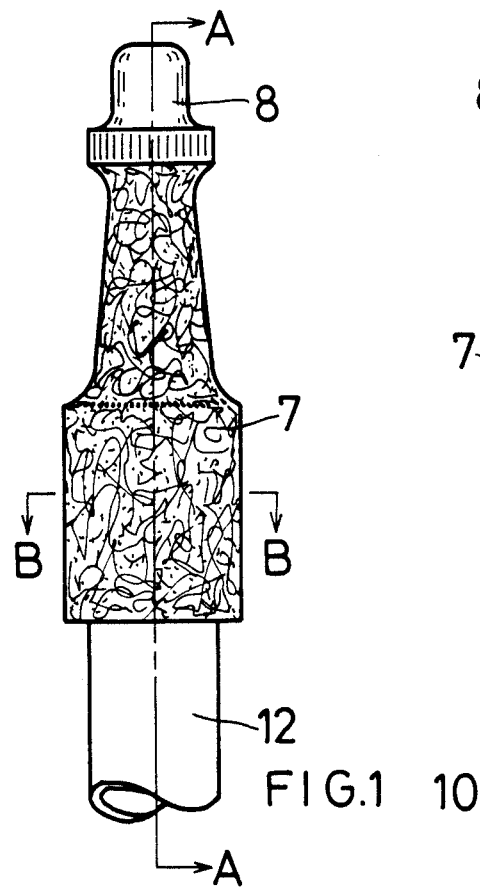
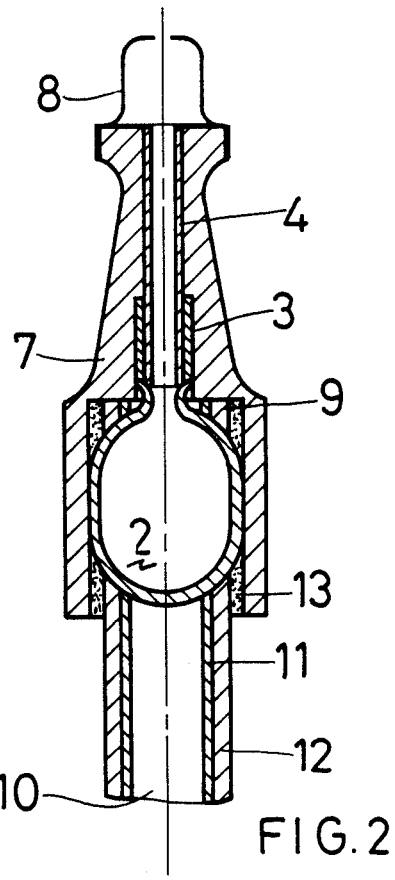
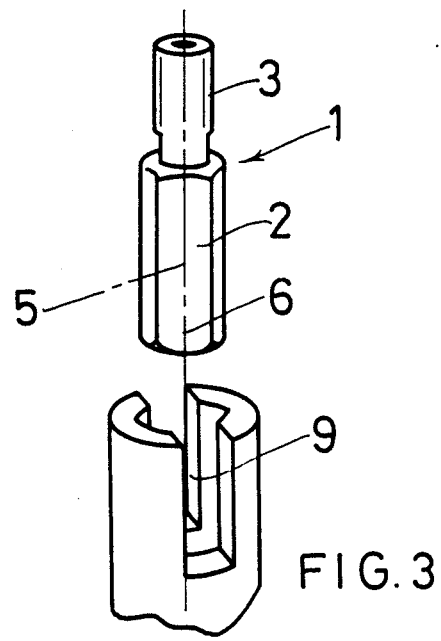
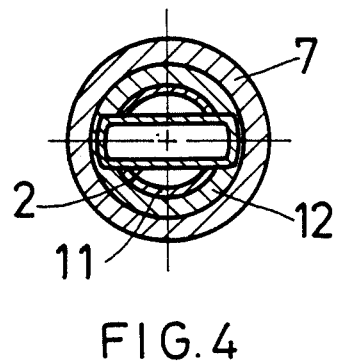

HOT METAL SAMPLING

BACKGROUND OF THE INVENTION

THIS INVENTION relates to the sampling of molten metals and more particularly to sampling such metals effected by immersion of a sampler into metals of both high and low temperatures.

Molten metal sampling using a long handled spoon dipped into molten metal has many disadvantages and has today been largely replaced by methods resulting in a sample of metal being obtained which is disc-shaped to provide a polished surface for spectrographic analysis, usually this sample is obtained along with what is known as a "classic" pin extending from the disc-shaped portion. Such a sample is obtained by dipping a mould consisting of a glass tube engaged in the inlet to a split metal mould into the melt. Molten metal is thereby caused to flow into the mould to fill it and the glass tube. The metal thus contained is removed and freezes in the mould and glass tube.

In order to immerse the mould it is usually held in the end of a thick walled cardboard tube surrounded by moulded sand. The mould is glued in position.

The cardboard tube is, in use, carried by a steel immersion lance which is protected by the cardboard.

A thin metal cap is located over the inlet end to the glass tube to enable the sampler to penetrate through the slag on top of the molten metal.

This type of sampler has certain inherent disadvantages which include the fact that the cardboard tube causes a reaction in contact with molten metal. This reaction can be violent and even dangerous. Resulting from this the sampler can generally only be immersed for a short period and to a limited depth into the molten metal bath.

Added to this is the further fact that there is frequently considerable difficulty in recovering the sample from the cardboard tube on removal from the molten metal.

It is the object of the present invention to provide a method and means for sampling hot metals which at least reduces the above difficulties.

SUMMARY OF THE INVENTION

According to this invention there is provided a method of sampling molten metal which comprises securing a sampling mould in the end of a tube having at least a layer of non-reactive refractory material and immersing the sampler so secured into the molten metal to recover the sample.

The invention also provides a sampler for such a method comprising a split metal mould located in a slot in the end of a tube having at least an outer layer of non-reactive refractory material and the mould encased in a body of non-reactive refractory material.

Further features of this invention provide for the body to be moulded from a refractory material having at least the exposed surface layers of glass or glass-forming materials. The glass or glass forming material layer, upon immersion in the molten metal, fills and welds closed any cracks which may result from the thermal shock on immersion.

The invention also provides for the metal mould to have one end of a glass tube projecting located in the inlet to the mould and for the glass tube also to be encased in the body of refractory material.

BRIEF DESCRIPTION OF THE DRAWINGS

An example of this invention will be described with reference to the accompanying drawings in which:

FIG. 1 is an elevation of the sampler,

FIG. 2 a cross section through FIG. 1 on the line A—A,

FIG. 3 illustrates the locations of the metal sampling mould in the tube and,

FIG. 4 a cross-section through FIG. 1 on the line B—B.

DETAILED DESCRIPTION WITH REFERENCE TO THE DRAWINGS

As shown the sampler comprises a split metal mould 1 of conventional form to provide a disc-shaped body and projecting inlet neck portion 3. In the example illustrated a glass tube 4 is located in the neck portion 3 so that the sample body will have a flat disc with a classic pin projecting therefrom.

The joint 5 between the parts of the split mould has venting apertures 6 provided therein.

The mould 1 is provided with an outer body 7 of non-reactive refractory material having a composition which will provide a glass or glass-like surface on immersion into molten metal. A thin metal cap 8 is fitted and retained over the open end of the glass tube 4.

The body 7 has a cavity formed therein so that the body portion 2 of the mould 1 may be located in a slot 9 formed in the end of a tube 10. This tube has at least an outer surface of non-reactive refractory material. Preferably the tube 10 will have a thin walled cardboard inner body 11 and an outer layer 12 of non-reactive refractory material. The composition of this material can be the same as that of the body 7. Also the tube will preferably be of the same dimensions as that used for holding standard thermocouples for temperature measurement of molten metals thus enabling these tubes to be used for either sampling or temperature measurement of molten metals.

Preferably the tube 10 is secured in the body 7 with the use of a suitable synthetic resin adhesive at 13.

The refractory material referred to above will include an antispalling agent. The body of refractory material can be applied as a base with the glassy or glass forming outer surface material applied as a separate layer. Alternatively the materials may be provided as a mixture which will form the glassy outer layer in use.

The glassy material layer may be obtained from powdered glass or glass forming constituents and the coating applied particularly to the cardboard in one or more layers in slurry form which are subsequently dried before use.

The refractory material and antispalling consituents may comprise of up to 15% aluminium oxide, zirconium oxide or a mixture thereof, up to 40% silicon oxide and up to 15% graphite, these and other proportions in this specification being by mass of the total material of the coating.

Also the glassy material layers may be obtained by mixing with refractory and antispalling constituents up to 75% glass powder or the mixture may include up to 5% of potassium of sodium oxide, or both and may also include in addition up to 5% of calcium oxide, magnesium oxide or lithium oxide proportions of these constituents.

Further the refractory and antispalling material, alone or mixed with other constituents may include a slurry viscosity controlling substance and a binder, these latter preferably being a suitable clay and sodium silicate in powder form. These latter constituents may be included in a proportion of up to 15% in total.

Finally it is preferred that the coating material include a flux such as fluorspar in a proportion of 1%.

Some examples of the mixtures according to the invention are as follows:

EXAMPLE 1

Glass flour, 65.65%
Zircon flour, 7.55%
Fluorspar, 1.00%
Carbon flour, 10.00%
Western Province Ball Clay, 7.50%
Lithium Carbonate, 0.03%
Lime, 0.77%
Sodium Silicate (2692), 7.50%

EXAMPLE 2

Glass flour, 58.10%
Zircon flour, 15.10%
Fluorspar, 1.00%
Carbon flour, 10.00%
Western Province Ball Clay, 7.50%
Lithium Carbonate, 0.03%
Lime, 0.77%
Sodium Silicate (2692) 7.50%

EXAMPLE 3

Glass flour 50,50%
Zircon flour, 22.70%
Fluorspar, 1.00%
Carbon flour, 10.00%
Western Province Ball Clay, 7.50%
Lithium Carbonate, 0.03%
Lime, 0.77%
Sodium Silicate (2692) 7.50%

EXAMPLE 4

Glass flour, 44.00%
Zircon flour, 29.20%
Fluorspar, 1.00%
Carbon flour, 10.00%
Western Province Ball Clay, 7.50%
Lithium Carbonate, 0.03%
Lime, 0.77%
Sodium Silicate (2692), 7.50%

EXAMPLE 5

Glass flour, 31.50%
Welding flux, 41.70%
Fluorspar, 1.00%
Carbon flour, 10.00%
Western Province Ball Clay, 7.50%
Lithium Carbonate, 0.03%
Lime, 0.77%
Sodium Silicate (2692), 7.50%

EXAMPLE 6

Soda ash, 11.70%
Zircon flour, 22.70%
Fluorspar, 1.00%
Carbon flour, 10,00%
Western Province Ball Clay, 7.50%
Lithium Carbonate, 0.03%
Lime, 0.77%
Sodium Silicate (2692), 7.50%
Recycled foundry sand, 38.80%

It will be understood that recycled foundry sand is sand having been previously contacted with sodium silicate, used in foundry processes and then cured with carbon dioxide.

EXAMPLE 7

Zircon flour, 21.05%
Andalusite flour, 10.53%
Glass flour, 26.32%
Welding flux, 5.26%
Carbon flour, 15.79%
Sodium Silicate (3379), 21.05%

The sodium silicate may be applied either in powdered or liquid form although the powdered form is preferable as this has been found to reduce blistering of the material.

It will be appreciated that all the above mentioned percentages relate to the total mass of the material. It will further be appreciated that the term flour implies that the substance is in a finely powdered or ground form having a particle size of the order of 100 microns or less.

EXAMPLE 8

Glass flour, 13.39%
Zircon flour, 15.62%
Carbon flour, 2.23%
Clay, 2.23%
Calcite or Lime, 0.45%
Fluorspar, 1.78%
Course Silica Sand, 53.55%
(approx. grain size 1mm)
Sodium Silicate (3379), 10.71%
Methocel (Plastisiser), 0.04%

In all examples sufficient water is used to obtain a slurry of convenient constituency or enable the coating process to be carried out.

Also it is to be noted that Example 8 is preferably used as a three layer coating. An initial sealing coat is applied to the base cardboard tubing followed by a coarse layer including the coarse silica sand and finally a glass forming layer is provided.

In use it has been found that sampling can be easily and effectively achieved because of the lack of any violent reaction when the sampler is immersed into molten metal. The sampler may be easily dipped to greater depths and for periods considerably longer than has heretofore been comfortably possible. Also the gases may escape from the mould directly through the tube 10.

Further the nature of the refractory material is such that the sample can be simply recovered by shattering the body 7 and end of the tube 10 when the sampler is retrieved from the melt.

The invention provides a simple assembly which enables conventional sampling to be effected expeditiously and effectively at low cost.

The term "non-reactive refractory material", as used conventionally and in this specification, means material which will avoid the violent reaction on immersion in molten metal that is usually encountered when a conventional cardboard tube for protecting a steel immersion lance is immersed in molten metal.

What I claim as new and desire to secure by Letters Patent is:

1. A sampler for sampling molten metal, comprising:
   a tube having at least an outer layer of non-reactive refractory material and a slot located in a first end thereof;
   a split metal mould located in said slot;
   said mould encased in a body of non-reactive refractory material covering the tube; and
   wherein the non-reactive refractory material of both the tube and the body comprises at least the exposed surfaces thereof a material which forms glass, or includes glass, so that upon immersion into the molten metal and resulting contact of the molten metal therewith, thermal shock is compensated for by the pre-existing or formed glass forming a layer filling and welding closed any cracks which may result from the thermal shock.

2. A sampler as recited in claim 1 wherein said metal mould has one end of a glass tube projecting from a neck portion thereof, located in the inlet to the mould; said glass tube also being encased in said body of refractory material.

3. A sampler as recited in claim 2 wherein the refractory material includes an antispalling agent.

4. A sampler as recited in claim 1 wherein the refractory material includes an antispalling agent.

5. A sampler as recited in claim 4 wherein said refractory material and antispalling constituents comprise an amount greater than 0 up to about 15% of material selected from the group consisting essentially of aluminum oxide, zirconium oxide, and a mixture of zirconium and aluminum oxides; an amount of silicon oxide greater than 0 and up to about 40%; and graphite in an amount of greater than 0 and up to about 15%.

6. A sampler as recited in claim 5 wherein said glassy material layer comprises a positive amount of material, up to about 5%, selected from the group consisting essentially of calcium oxide, magnesium oxide, lithium oxide, and mixtures of calcium, magnesium, and/or lithium oxide.

7. A sampler as recited in claim 4 wherein said glassy material layer comprises a mixture of refractory and antispalling constituents containing potassium or sodium oxide, and glass powder.

8. A sampler as recited in claim 7 wherein the amount of glass powder comprises a positive amount up to about 75%, and wherein the amount of potassium and/or sodium oxide comprises an amount greater than 0 and up to about 5%.

9. A sampler as recited in claim 1 wherein said body comprises a base layer of refractory material, and an exposed surface layer applied as a separate layer and comprising said glass or glass forming materials.

10. A sampler as recited in claim 9 wherein said material for said glassy outer surface layer comprises powdered glass or glass forming constituents.

11. A sampler as recited in claim 1 wherein said refractory material which forms said glassy outer surface layer comprise a mixture for the whole body of refractory material.

12. A sampler as recited in claim 9 further comprising an intermediate layer of coarse silica sand.

13. A method of sampling molten metal utilizing a sampler comprising a tube having a slot in a first end thereof, and having an outer layer of non-reactive refractory material, and a split metal mould encased in a body of non-reactive refractory material, with the non-reactive refractory material of the tube and the body comprising, at at least exposed layers thereof, glass or glass forming materials, comprising the steps of:
   immersing the sampler into the molten metal so that a violent reaction does not occur, and the glass or glass forming materials fill and weld closed any cracks which may result from the thermal shock on immersion;
   collecting a sample; and
   removing the sample from the molten metal.

* * * * *